(12) United States Patent
Allen et al.

(10) Patent No.: US 6,923,952 B2
(45) Date of Patent: *Aug. 2, 2005

(54) ENHANCED EFFICACY ANTIPERSPIRANT COMPOSITIONS CONTAINING STRONTIUM OR CALCIUM

(75) Inventors: Jan L. Allen, Silver Spring, MD (US); Yan-Fei Shen, Canton, MA (US)

(73) Assignee: The Gillette Company, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/641,305

(22) Filed: Aug. 14, 2003

(65) Prior Publication Data

US 2005/0036967 A1 Feb. 17, 2005

(51) Int. Cl.[7] ............................. A61K 7/32; A61K 7/34; A61K 7/38
(52) U.S. Cl. ............................. 424/65; 424/66; 424/68; 424/400; 424/401
(58) Field of Search .............................. 424/65, 66, 68, 424/400, 401

(56) References Cited

U.S. PATENT DOCUMENTS

| 5,716,625 A | 2/1998 | Hahn et al. ................. 424/401 |
| 5,788,956 A | 8/1998 | De Lacharriere et al. ..... 424/65 |
| 5,804,203 A | 9/1998 | Hahn et al. ................. 424/401 |
| 5,900,257 A | 5/1999 | Breton et al. ................ 424/639 |
| 5,958,436 A | 9/1999 | Hahn et al. ................. 424/401 |
| 5,972,892 A | 10/1999 | De Lacharriere et al. ..... 514/15 |
| 6,042,816 A | 3/2000 | Shen ........................... 424/65 |
| 6,139,850 A | 10/2000 | Hahn et al. ................. 424/401 |
| 6,342,210 B1 | 1/2002 | Cai et al. |
| 6,375,938 B1 | 4/2002 | Clothier, Jr. et al. |
| 6,403,069 B1 | 6/2002 | Chopra et al. |
| 6,436,381 B1 | 8/2002 | Carrillo et al. |
| 2003/0211060 A1 | 11/2003 | Yin et al. ..................... 424/66 |
| 2004/0091436 A1 | 5/2004 | Li et al. |

OTHER PUBLICATIONS

U.S. Appl. No. 10/641,348, (Yan–Fei Shen).

*Primary Examiner*—Shelley A. Dodson
(74) *Attorney, Agent, or Firm*—Stephen P. Williams

(57) ABSTRACT

Disclosed are enhanced efficacy antiperspirant compositions containing a strontium salt and/or a calcium salt. In particular, there is disclosed an antiperspirant composition comprising a dermatologically acceptable carrier vehicle, about 8% to about 22% (USP) of an aluminum-zirconium chlorohydrate-gly antiperspirant salt, wherein the antiperspirant salt has an HPLC peak 5 area of at least 33%, and about 0.5% to about 15%, preferably about 1% to about 6%, by weight, of a water soluble salt selected from the group consisting of a water soluble strontium salt, a water soluble calcium salt and a mixture thereof. It has been found that the inclusion of a strontium salt and/or a calcium salt boosts the efficacy of a high peak 5 antiperspirant salt. As a preferred feature, the antiperspirant salt and the water soluble salt are dissolved in at least a portion of the carrier vehicle.

14 Claims, No Drawings

# ENHANCED EFFICACY ANTIPERSPIRANT COMPOSITIONS CONTAINING STRONTIUM OR CALCIUM

BACKGROUND OF THE INVENTION

The present invention relates to enhanced efficacy antiperspirant compositions containing a strontium salt and/or a calcium salt.

Enhanced efficacy aluminum and aluminum-zirconium antiperspirant salts are well known and are described, for example, in GB 2,048,229 and U.S. Pat. No. 4,775,528. These salts are generally made by heat treating a relatively dilute solution of the salt (e.g., about 10% by weight) to increase its HPLC peak 4 to peak 3 ratio, then spray drying to a powder. These salts typically have an HPLC peak 4 to peak 3 area ratio of 0.7 or higher, with at least 70% of the aluminum contained in said peaks. However, these enhanced salts are also known to rapidly revert back to their non-enhanced state (for example, as evidenced by an HPLC peak 4 to peak 3 area ratio of 0.3 or less) in aqueous solution, particularly at concentrations greater than 20%. Consequently, the enhanced antiperspirant salts are generally only available in powder form. Moreover, the enhanced salts are generally only formulated into finished formulations as suspended powders in order to retain their enhanced efficacy.

In U.S. Pat. No. 6,042,816, there are described enhanced efficacy antiperspirant salts (with peak 4:3>0.5) that are stable in aqueous solution. These salts include a soluble calcium salt such as calcium chloride and a soluble amino acid such as glycine. Typically, these salts have a Ca:Al+Zr weight ratio of about 1:1 to about 1:28 and an amino acid:Al+Zr weight ratio of about 2:1 to about 1:20. Because these salts retain their enhanced efficacy in aqueous solution (as evidenced by retention of their high peak 4:3 ratio), they have an advantage over conventional enhanced efficacy salts that revert to the non-enhanced form in aqueous solution. In U.S. Pat. No. 5,955,065, there are described anhydrous antiperspirant compositions that include a suspended antiperspirant salt, such as an enhanced efficacy aluminum-zirconium tetrachlorohydrex-gly (with peak 4:3>0.5), and a water soluble calcium salt, typically in an amount of about 0.5% to 15%.

In U.S. Pat. No. 5,804,203, there are described topical compositions that contain an irritant ingredient (e.g., organic alcohol, carboxylic acid, keto acid, peroxide, etc.), an anti-irritant divalent strontium cation, and a cosmetic or therapeutic active ingredient. The strontium cation is said to reduce skin irritation that would otherwise result from the irritant ingredient. Example 11 illustrates an antiperspirant composition that includes aluminum chlorohydrate, ethanol and strontium nitrate. This composition does not include an amino acid or a zirconium salt. In U.S. Pat. No. 5,958,436, there are described topical compositions that contain an irritant ingredient (e.g., organic alcohol, carboxylic acid, keto acid, peroxide, etc.), and an anti-irritant divalent calcium cation. The calcium cation is said to reduce skin irritation that would otherwise result from the irritant ingredient.

In U.S. Pat. No. 5,788,956, it is suggested that perspiration can be controlled by topically applying a substance P antagonist. Various substance P antagonists are disclosed including peptide and non-peptide nitrogenous derivatives and salts of monovalent, divalent and trivalent cations. The latter includes strontium, magnesium, cobalt, nickel, manganese, barium, etc. Examples 1, 3 and 4 of the patent disclose compositions containing strontium chloride or strontium nitrate. However, the patent does not provide any sweat reduction data for the exemplified compositions. In contrast to the suggestion in this patent, the present applicant found that a clear gel product containing 5% strontium nitrate does not provide any measurable sweat reduction (see Example 1, test product "Comp.1", infra).

Recently, a new type of enhanced efficacy aluminum-zirconium antiperspirant salt is described in U.S. Pat. No. 6,436,381, which is incorporated herein by reference. These salts, when analyzed by HPLC as a 10% aqueous solution using conditions capable of resolving the aluminum into at least four successive peaks (conveniently labeled peaks 2 to 5), exhibit an HPLC peak 5 area of at least 33% or more, preferably at least 45%, based on the total area of HPLC peaks 2 to 5. That is, the salts have a high peak 5 Al content. These salts also typically have a low metal (Al+Zr) to chloride (or anion) ratio, for example, between 0.90 and 1.00. These high peak 5 enhanced efficacy salts, hereinafter referred to as "$E^5$AZCH", may have greater efficacy, in some applications, than the previously known enhanced efficacy aluminum-zirconium salts with high peak 4 content (i.e., peak 4>30% or peak 4:3>0.7 and peak 5<25%).

It would be highly desirable to provide enhanced efficacy antiperspirant compositions with superior efficacy, in particular, with higher efficacy than is currently obtained with the aforementioned $E^5$AZCH salts.

SUMMARY OF THE INVENTION

The present invention embraces enhanced efficacy antiperspirant compositions containing a strontium salt and/or a calcium salt. In one embodiment, the invention embraces an antiperspirant composition comprising a dermatologically acceptable carrier vehicle, about 8% to about 22% (USP) of an aluminum-zirconium chlorohydrate-gly antiperspirant salt, wherein the antiperspirant salt has an HPLC peak 5 area of at least 33%, and about 0.5% to about 15%, preferably about 1% to about 6%, by weight, of a water soluble salt selected from the group consisting of a water soluble strontium salt, a water soluble calcium salt and a mixture thereof. It has been found that the inclusion of a strontium salt and/or a calcium salt boosts the efficacy of a high peak 5 antiperspirant salt. As a preferred feature, the antiperspirant salt and the water soluble salt are dissolved in at least a portion of the carrier vehicle. In a more preferred embodiment, the carrier vehicle will comprise water. In another embodiment, the carrier vehicle may comprise a polyhydric alcohol.

In a further embodiment, the invention embraces an antiperspirant composition comprising, by weight, about 8% to about 42% (USP) of an aluminum-zirconium chlorohydrate-gly antiperspirant salt, wherein the antiperspirant salt has an HPLC peak 5 area of at least 33%, about 0.5% to about 15% of a water soluble salt selected from the group consisting of a water soluble strontium salt, a water soluble calcium salt and a mixture thereof, and about 15% to about 90% water, wherein the antiperspirant salt and the water soluble salt are dissolved in the water. As a preferred feature, this composition may additionally comprise an oil, such as a volatile silicone, and may be in the form of a water-in-oil emulsion.

DETAILED DESCRIPTION OF THE INVENTION

The compositions of the present invention include an enhanced efficacy aluminum-zirconium antiperspirant salt with a high peak 5 aluminum content. These salts are more fully described in U.S. Pat. No. 6,436,381, which is incorporated herein by reference. These salts, when analyzed by HPLC as a 10% aqueous solution using conditions capable of resolving the aluminum into at least four successive peaks (conveniently labeled peaks 2 to 5), exhibit an HPLC peak 5 area of at least 33% or more, preferably at least 45%, based on the total area of HPLC peaks 2 to 5. The preferred salts include the aluminum-zirconium chlorohydrates, which have an Al:Zr ratio of about 2 to about 10 and a metal (Al+Zr) to chloride ratio (M:Cl) of about 0.9 to about 2.1. The high peak 5 aluminum-zirconium chlorohydrates (hereinafter referred to as "E$^5$AZCH") typically have a low metal to chloride ratio, for example, between about 0.90 and about 1.10, preferably between about 0.90 and about 1.00. In addition, the aluminum-zirconium chlorohydrates also include an amino acid, such as glycine, associated with them to prevent polymerization of the zirconium species and reduce skin irritation by raising the pH. Thus, the preferred antiperspirant salts are referred to as aluminum-zirconium chlorohydrate-gly or, alternatively, aluminum-zirconium chlorohydrex-gly (hereinafter abbreviated as "E$^5$AZCH-Gly").

The preferred aluminum-zirconium chlorohydrate-gly antiperspirant salts generally have the empirical formula $Al_nZr(OH)_{[3n+4-m(n+1)]}(Cl)_{[m(n+1)]}(Gly)_q$ where n is 2.0 to 10.0, preferably 3.0 to 8.0, and m is about 0.91 to about 1.11 (which corresponds to M:Cl=1.1–0.9), preferably about 1.00 to about 1.11 (which corresponds to M:Cl=1.0–0.9), and q is about 0.8 to about 4.0, preferably about 1.0 to 2.0. Optionally, glycine ("Gly") may be replaced by another amino acid such as alanine, valine, serine, leucine, or aminobutyric acid, although glycine is preferred. In addition to having a high peak 5 content, the most preferred salts will also have an HPLC peak 4 to peak 3 area ratio of at least 0.5.

The compositions of the present invention include a water soluble salt comprising a water soluble strontium salt and/or a water soluble calcium salt. By soluble is meant those salts which are soluble in water or which dissolve in an aqueous solution of antiperspirant salt. Preferred strontium salts include strontium chloride, strontium bromide, strontium nitrate, strontium citrate, strontium formate, strontium acetate, strontium gluconate, strontium ascorbate, strontium lactate, strontium glycinate and mixtures thereof. Although not preferred, strontium carbonate, strontium sulfate and strontium hydroxide may also be used because they will dissolve in an aqueous solution of the antiperspirant salt. Preferred calcium salts include calcium chloride, calcium bromide, calcium nitrate, calcium citrate, calcium formate, calcium acetate, calcium gluconate, calcium ascorbate, calcium lactate, calcium glycinate and mixtures thereof. Although not preferred, calcium carbonate, calcium sulfate and calcium hydroxide may also be used because they will dissolve in an aqueous solution of the antiperspirant salt.

The amount of water soluble salt utilized may vary within a wide range and will typically comprise about 0.5% to about 15%, preferably about 1% to about 10%, more preferably about 2% to about 6%, by weight, of the composition. When the composition includes a higher level of antiperspirant salt, for example about 20% to about 42% (USP), then it should also include a higher level of water soluble salt, typically about 3% to about 15%, more typically about 5% to about 10%. When the composition includes a lower level of antiperspirant salt, for example about 8% to about 22% (ASP), then it should also include a lower level of water -soluble salt, typically about 0.5% to about 10%, more typically about 1% to about 6%.

In addition to the antiperspirant salt and the water soluble salt, the composition of the present invention also includes a dermatologically acceptable carrier vehicle. The carrier vehicle may be any of those vehicle components typically used in topical antiperspirant compositions such as, for example, water, alcohol, polyhydric alcohol, organic oil, silicone oil, etc., as well as various other optional cosmetic ingredients typically used to improve the aesthetic properties of the topical composition, such as, for example, fragrances, emollients, wash-off agents, gelling agents, etc. Although the antiperspirant salt and the water soluble salt may be suspended (e.g., in powder form) in an anhydrous carrier vehicle, preferred compositions of the present invention will have both the antiperspirant salt and the water soluble salt dissolved in at least one portion of the carrier vehicle. Preferably the carrier vehicle will comprise water, alcohol or polyhydric alcohol, or a mixture of at least two of these, and the antiperspirant salt and the water soluble salt will be dissolved therein. More preferably the carrier vehicle will comprise water (either as the sole vehicle or in addition to other vehicle components) and the antiperspirant salt and the water soluble salt will be dissolved therein.

Thus, a suitable antiperspirant composition may comprise, by weight, about 8% to about 42% (USP) of the high peak 5 antiperspirant salt, about 0.5% to about 15% of the water soluble strontium and/or calcium salt and about 10% to about 90%, preferably about 15% to about 80%, water. When such a composition is formulated in concentrated form, such as for bulk shipment to finished goods manufacturers who will add the concentrated form as a component to a finished formulation, it will typically comprise about 20% to about 42% (USP) of the antiperspirant salt, about 3% to about 15%, preferably about 5% to about 10%, of the water soluble salt, and about 25% to about 75% water. Finished topical formulations will generally comprise about 8% to about 22% (USP) of the antiperspirant salt, about 0.5% to about 10%, preferably about 1% to about 6%, of the water soluble salt, and about 10% to about 50% water.

The antiperspirant compositions of the present invention may be formulated into finished topical compositions such as liquids (e.g., for roll-on or porous applicators), lotions, creams, gels, soft-solids, solid sticks, etc. In particular, when the compositions are aqueous solutions, as described above, they may be utilized in oil-in-water and water-in-oil emulsions, such as the currently popular clear gel formulations (as described, for example, in U.S. Pat. No. 5,587,153). When formulated as an emulsion (e.g., a water-in-oil emulsion), the composition will comprise, in addition to the water, antiperspirant salt and water soluble salt, an oil such as an organic oil and/or a silicone oil, particularly a volatile silicone. Of course, the aforementioned aqueous solutions also may be used in other aqueous based compositions such as aqueous or aqueous-alcoholic based roll-ons.

In addition to the above-described aqueous solutions, the present invention also includes compositions comprising the antiperspirant salt, the water soluble strontium and/or calcium salt, and a liquid polyhydric alcohol, wherein the antiperspirant salt and the water soluble salt are dissolved in the polyhydric alcohol. The liquid polyhydric alcohol will typically have from three to six carbon atoms and from two to six hydroxyl groups, such as, for example, propylene glycol and dipropylene glycol. Compositions of this type can be readily formulated into topical antiperspirant compositions which use a polyhydric alcohol vehicle, such as clear sticks gelled with dibenzylidene sorbitol or other gellants (see, for example, U.S. Pat. No. 5,705,171).

The present invention may be further illustrated by the following examples in which the parts and percentages are by weight. The abbreviation E⁵AZCH-Gly, when used in the examples, means an enhanced efficacy aluminum-zirconium chlorohydrate-gly having an HPLC peak 5 area greater than 40% and a metal (Al+Zr) to chloride ratio between 0.9 and 1.0. This salt was made in accordance with the procedure set out in U.S. Pat. No. 6,436,381.

EXAMPLE 1

Antiperspirant gel compositions comprising the following ingredients, in which all parts and percentages are by weight, were prepared in the following manner. The water phase components (E⁵AZCH-Gly, $Sr(NO_3)_2$ (when present) propylene glycol, ethanol, water, alcloxa (when present) and glycine (when present)) and the oil phase components (dimethicone and dimethicone copolyol) are each mixed in separate containers and filtered. The water phase is then slowly added to the oil phase with sufficient mixing to form an emulsion with minimum aeration. This emulsion is then sheared in a homogenizer to form a gel with a viscosity of about 120,000 to 160,000 cP (120–160 Pas).

|  | Weight Percent | | |
|---|---|---|---|
| Ingredient | Ex. 1 | Comp. 1 | Comp. 2 |
| Water | 42.3 | 45.1 | 47.0 |
| E⁵ACZH-Gly | 18.4[1] | 18.4[1] | |
| $Sr(NO_3)_2$ | 5.0 | | 5.0 |
| Ethanol | 9.4 | 10.0 | 10.4 |
| Propylene Glycol | 7.6 | 8.1 | 10.6 |
| Dimethicone (DC 225) | 9.1 | 9.7 | 10.1 |
| Dimethicone Copolyol (DC-3225C) | 8.2 | 8.7 | 8.4 |
| Glycine | | | 8.0 |
| Alcloxa | | | 0.5 |

[1]Corresponds to approximately 14% USP

The test product of Ex. 1 (with strontium salt) was tested for thermal efficacy (i.e., hot room sweat reduction) versus the control product of Comp. 1 (without strontium salt) on female panelists in a standard hot room panel study (AvB; test product applied to one axilla and control product applied to other axilla). The test product provided a 12% improvement in thermal efficacy-versus the control and this result was highly significant on a statistical basis. In a similar, but separate test, the product of Comp. 2 (with strontium salt, but no antiperspirant salt) was found to provide no sweat reduction. Thus, it was concluded that the strontium salt, alone, does not have antiperspirant efficacy.

EXAMPLES 2–6

Antiperspirant compositions are made with the ingredients and amounts listed in the following table.

|  | Weight Percent | | | | |
|---|---|---|---|---|---|
| Ingredient | Ex. 2 | Ex. 3 | Ex. 4 | Ex. 5 | Ex. 6 |
| Water | 65.0 | 60.0 | 65.0 | 60.0 | 64.0 |
| E⁵ACZH-Gly | 30.0 | 30.0 | 30.0 | 30.0 | 30.0 |
| $Sr(NO_3)_2$ | 5.0 | 10.0 | | | 3.0 |
| $CaCl_2$ | | | 5.0 | 10.0 | 3.0 |

These compositions may be used to formulate topical antiperspirant compositions such as aqueous solutions, aqueous-alcoholic solutions and water-in-oil emulsions and will provide extremely high antiperspirant efficacy.

Throughout the specification reference to HPLC analysis means that chromatograms were obtained as follows: Salt solutions are evaluated for aluminum polymer distribution by HPLC at a concentration of about 10% Al or Al-Zr salt. If the solution to be analyzed is at a higher salt concentration, it is diluted with sufficient water to bring the salt concentration to about 10%. A 1.0 µL sample is pumped through a 4.6 mm×50 cm column packed with Nucleosil 100-5 (Keystone Scientific Inc.) using a 0.01M aqueous nitric acid solution as the eluent. The flow rate of the mobile phase was controlled at 0.5 mL/min with a Waters 100 unit. HPLC profiles were recorded and processed with a computerized system that included the Millennium 2010 Chromatography Manager software from the Millipore/Waters Corp. A Waters 410 differential refractometer was used as the refractive index detector. The HPLC profiles are read from left to right (higher to lower molecular weight). Following this technique, peaks 3, 4 and 5 generally appear at retention times of about 9.2 to about 10.0 minutes, about 10.5 to about 11.2 minutes, and about 11.8 to about 12.5 minutes respectively. Naturally, of course, other HPLC techniques which use different column materials, eluents and flow rates can be used provided that they sufficiently resolve peaks 2, 3, 4 and 5 with an acceptable degree of precision (i.e., the technique must be capable of resolving the Al into at least four distinct peaks). Obviously, other techniques may place peaks 3, 4 and 5 at different retention times from those given above.

It should be noted that reference throughout this application to weight percent of antiperspirant salt is intended to be calculated as anhydrous weight percent in accordance with the U.S.P. method. This calculation excludes any bound water and glycine. For aluminum-zirconium chlorohydrate, the calculation is as follows:

$$\% \text{ AZCH} = \% \text{ Al}\{26.98y + 92.97 + 17.01[3y+4-(y+1)/z] + 35.45(y+1)/z\}/26.98y$$

where y=Al/Zr ratio and z=metal/Cl ratio.
For reference purposes, calculation of antiperspirant salt weight percent in accordance with the U.S.P. method compares to the previously used standard industry method as follows: 50% AZCH (std)≅38.5% USP.

What is claimed is:

1. An antiperspirant composition comprising a dermatologically acceptable carrier vehicle, about 8% to about 22% (USP) of an aluminum-zirconium chlorohydrate-gly antiperspirant salt, wherein said antiperspirant salt has an HPLC peak 5 area of at least 33%, and about 0.5% to about 15%, by weight, of a water soluble salt selected from the group consisting of a water soluble strontium salt, a water soluble calcium salt and a mixture thereof wherein the antiperspirant salt and the water soluble salt are dissolved in at least a portion of the carrier vehicle.

2. The composition of claim 1 wherein the carrier vehicle comprises water and the antiperspirant salt and the water soluble salts are dissolved in water. antiperspirant salt and the water soluble salt are suspended in the carrier vehicle.

3. An antiperspirant composition comprising, by weight, about 8% to about 42% (USP) of an aluminum-zirconium chlorohydrate-gly antiperspirant salt, wherein said antiperspirant salt has an HPLC peak 5 area of at least 33%, about 0.5% to about 15% of a water soluble salt selected from the group consisting of a water soluble strontium salt, a water soluble calcium salt and a mixture thereof, and about 10% to about 90% water, wherein the antiperspirant salt and the water soluble salt are dissolved in the water.

4. The antiperspirant composition of claim 3 comprising about 20% to about 42% (USP) of said antiperspirant salt, about 3% to about 15% of said water soluble salt, and about 25% to about 75% water.

5. The antiperspirant composition of claim 3 comprising about 8% to about 22% (USP) of said antiperspirant salt, about 0.5% to about 10% of said water soluble salt, and about 10% to about 50% water.

6. The antiperspirant composition of claim 3 wherein said antiperspirant salt has an HPLC peak 4 to peak 3 area ratio of at least 0.5.

7. The antiperspirant composition of claim 3 wherein said antiperspirant salt has an HPLC peak 5 area of at least 45%.

8. The antiperspirant composition of claim 2, 3, 4, 5, 6, or 7, wherein said water soluble salt comprises a strontium salt.

9. The antiperspirant composition of claim 8 wherein said strontium salt is selected from the group consisting of strontium chloride, strontium bromide, strontium nitrate, strontium citrate, strontium formate, strontium acetate, strontium gluconate, strontium ascorbate, strontium lactate, strontium glycinate, and mixtures thereof.

10. The antiperspirant composition of claim 2, 3, 4, 5, 6, or 7 wherein said water soluble salt comprises a calcium salt.

11. The antiperspirant composition of claim 10 wherein said calcium salt is selected from the group consisting of calcium chloride, calcium bromide, calcium nitrate, calcium citrate, calcium formate, calcium acetate, calcium gluconate, calcium ascorbate, calcium lactate, calcium glycinate, and mixtures thereof.

12. The antiperspirant composition of claim 3 additionally comprising an oil, wherein the composition is in the form of a water-in-oil emulsion.

13. The antiperspirant composition of claim 12 wherein the oil comprises a volatile silicone.

14. The composition of claim 1 wherein the carrier vehicle comprises a polyhydric alcohol and the antiperspirant salt and the water soluble salt are dissolved therein.

* * * * *

UNITED STATES PATENT AND TRADEMARK OFFICE
CERTIFICATE OF CORRECTION

PATENT NO. : 6,923,952 B2
DATED : August 2, 2005
INVENTOR(S) : Jan L. Allen et al.

It is certified that error appears in the above-identified patent and that said Letters Patent is hereby corrected as shown below:

Column 6,
Line 50, after "thereof" insert a comma -- , --.
Line 55, replace "salts" with -- salt --; insert -- the -- before "water".
Lines 55-56, delete "antiperspirant salt and the water soluble salt are suspended in the carrier vehicle.".

Column 7,
Line 12, after "claim" insert -- 1, --.

Column 8,
Line 1, after "claim" insert -- 1, --.

Signed and Sealed this

Sixth Day of December, 2005

JON W. DUDAS
*Director of the United States Patent and Trademark Office*